United States Patent
Weber et al.

(10) Patent No.: US 8,398,693 B2
(45) Date of Patent: Mar. 19, 2013

(54) ELECTRICALLY ACTUATED MEDICAL DEVICES

(75) Inventors: Jan Weber, Maple Grove, MN (US); Tracee Eidenschink, Wayzata, MN (US); David Elizondo, Champlin, MN (US); Loren Simer, Minnetonka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 743 days.

(21) Appl. No.: 10/763,825

(22) Filed: Jan. 23, 2004

(65) Prior Publication Data

US 2005/0165439 A1 Jul. 28, 2005

(51) Int. Cl.
*A61F 2/06* (2006.01)

(52) U.S. Cl. ........................................... 623/1.11

(58) Field of Classification Search .............. 623/1.11, 623/1.18, 1.2, 1.34, 1.49, 3.11, 1.12; 606/191, 606/192–194; 604/509, 96.01–103.14
See application file for complete search history.

(56) References Cited

U.S. PATENT DOCUMENTS

| | | | |
|---|---|---|---|
| 4,793,359 A * | 12/1988 | Sharrow | 600/435 |
| 4,830,023 A | 5/1989 | de Toledo et al. | 128/772 |
| 5,100,933 A | 3/1992 | Tanaka et al. | 523/300 |
| 5,250,167 A | 10/1993 | Adolf et al. | 204/299 R |
| 5,268,082 A | 12/1993 | Oguro et al. | 204/282 |
| 5,389,222 A | 2/1995 | Shahinpoor | 204/299.2 |
| 5,556,700 A | 9/1996 | Kaneto et al. | 428/332 |
| 5,631,040 A | 5/1997 | Takuchi et al. | 427/100 |
| 5,766,013 A | 6/1998 | Vuyk | 434/114 |
| 5,855,565 A * | 1/1999 | Bar-Cohen et al. | 604/104 |
| 6,109,852 A | 8/2000 | Shahinpoor et al. | 414/1 |
| 6,117,296 A | 9/2000 | Thomson | 204/607 |
| 6,249,076 B1 | 6/2001 | Madden et al. | 310/363 |
| 6,391,051 B2 | 5/2002 | Sullivan, III et al. | 623/1.12 |
| 6,475,639 B2 | 11/2002 | Shahinpoor et al. | 428/614 |
| 6,514,237 B1 * | 2/2003 | Maseda | 604/533 |
| 6,520,983 B1 | 2/2003 | Colgan et al. | 623/1.11 |
| 6,583,533 B2 | 6/2003 | Kornbluh et al. | 310/309 |
| 6,586,859 B2 | 7/2003 | Kornbluh et al. | 310/309 |
| 6,679,836 B2 * | 1/2004 | Couvillon, Jr. | 600/146 |
| 6,969,395 B2 * | 11/2005 | Eskuri | 606/200 |

(Continued)

FOREIGN PATENT DOCUMENTS

| | | |
|---|---|---|
| GB | 2 227 020 A | 7/1990 |
| WO | WO 01/58973 A2 | 8/2001 |

(Continued)

OTHER PUBLICATIONS

Jager, Edwin W.H., et al., "Applications of Polypyrrole Microactuators," SPIE Proceedings, Conference on Electroactive Polymer Actuators and Devices, Mar. 1999, vol. 3669, pp. 377-384.

(Continued)

*Primary Examiner* — Thomas McEvoy
(74) *Attorney, Agent, or Firm* — Seager, Tuft & Wickhem LLC

(57) ABSTRACT

The present invention relates to medical devices for implantation or insertion into body lumens, for example, catheters, guidewires, stents and aneurysm coils. The devices of the present invention comprise electrically actuated materials, such as electroactive polymers and piezoelectric and electrostrictive materials, which enhance or expand their functionality.

7 Claims, 14 Drawing Sheets

U.S. PATENT DOCUMENTS

| | | | |
|---|---|---|---|
| 7,331,969 B1* | 2/2008 | Inganas et al. | 606/143 |
| 7,338,509 B2* | 3/2008 | Mattison | 606/192 |
| 2001/0026165 A1 | 10/2001 | Pelrine et al. | 324/750 |
| 2002/0039620 A1 | 4/2002 | Shahinpoor et al. | 427/2.12 |
| 2002/0133223 A1* | 9/2002 | Vito et al. | 623/1.18 |
| 2003/0236445 A1 | 12/2003 | Couvillon, Jr. | 600/114 |
| 2003/0236531 A1* | 12/2003 | Couvillon, Jr. | 606/113 |
| 2004/0024441 A1 | 2/2004 | Bertolino et al. | 623/1.12 |
| 2005/0102017 A1* | 5/2005 | Mattison | 623/1.11 |
| 2005/0149176 A1* | 7/2005 | Heggestuen et al. | 623/1.46 |
| 2007/0088256 A1* | 4/2007 | Intoccia | 604/102.02 |

FOREIGN PATENT DOCUMENTS

| | | |
|---|---|---|
| WO | WO 03/094800 A2 | 11/2003 |
| WO | WO 2004/000141 A1 | 12/2003 |

OTHER PUBLICATIONS

Otero, Toribio et al., "EAP as Multifunctional and Biomimetic Materials," SPIE Proceedings, Conference on Electroactive Polymer Actuators and Devices, Mar. 1999, vol. 3669, pp. 26-34.

Smela, Elisabeth, "Conjugated Polymer Actuators for Biomedical Applications," *Advanced Materials*, vol. 15, No. 6, Mar. 17, 2003, pp. 481-494.

Gülch, Ranier W., et al., "Characterization of Electroactive Behavior and of Progress in Developments and Applications of Ionic Polymer Gels," *Smart Structures and Materials 2002*, ed. Y. Bar-Cohen, SPIE Proceedings, vol. 4695, 2002, pp. 367-377.

Bar-Cohen, Yoseph, "Electroactive Polymers as Artificial Muscles—Capabilities, Potentials and Challenges," Sec. 11 in chap. 8 of *Handbook on Biomimetics*, ed. Yoshihito Osada (NTS, Inc., 2000), pp. 1-13.

Wax, S.G., et al., "Compliant Actuators Based on Electroactive Polymers," Materials Research Society Symposium Proceedings, vol. 600, 2000, pp. 3-11.

Rocchia, W., et al., "Exploiting Conducting Polymer Radial Expansion for Bioinspired Actuation," *Smart Structures and Materials 2003*, ed. Y. Bar-Cohen, SPIE Proceedings, vol. 5051, 2003, pp. 453-457.

Sahoo, Hemantkumar, et al., "Actuators Based on Electroactive Polymers," *Current Science*, vol. 81, No. 7, Oct. 2001, pp. 743-746.

Sansiñena, José-Maria, et al., "Conductive Polymers," Chap. 7 in *Electroactive Polymer Actuators (EAP) as Artificial Muscles*, ed. Y. Bar-Cohen (SPIE Press, 2001), pp. 193-221.

Bar-Cohen, Yoseph, ed., *WorldWide ElectroActive Polymers EAP (Artificial Muscles) Newsletter*, vol. 3, No. 1, Jun. 2001.

Bar-Cohen, Yoseph, "EAP History, Current Status, and Infrastructure," Chap. 1 in *Electroactive Polymer Actuators (EAP) as Artificial Muscles*, ed. Y. Bar-Cohen (SPIE Press, 2001), pp. 3-43.

Kornbluh, Roy, et al., "Application of Dieelectric Elastomer EAP Actuators," Chap. 16 in *Electroactive Polymer Actuators (EAP) as Artificial Muscles*, ed. Y. Bar-Cohen (SPIE Press, 2001), pp. 457-495.

Bar-Cohen, Yoseph, "Transition of EAP Material from Novelty to Practical Applications—Are We There Yet?" *Smart Structures and Materials 2001*, ed. Y. Bar-Cohen, SPIE Proceedings, vol. 4329, 2001, pp. 1-6.

Pelrine, Ron, et al., "Applications of Dielectric Elastomer Actuators," *Smart Structures and Materials 2001*, ed. Y. Bar-Cohen, SPIE Proceedings, vol. 4329, 2001, pp. 335-349.

Madden, John D.W., et al., "Polyprrole Actuators: Modeling and Performance," *Smart Structures and Materials 2001*, ed. Y. Bar-Cohen, SPIE Proceedings, vol. 4329, 2001, pp. 72-83.

Bar-Cohen, Yoseph, "EAP Applications, Potential, and Challenges," Chap. 21 in *Electroactive Polymer Actuators (EAP) as Artificial Muscles*, ed. Y. Bar-Cohen (SPIE Press, 2001), pp. 615-659.

Jager, Edwin W.H., et al., "Microfabricating Conjugated Polymer Actuators," *Science*, vol. 290, Nov. 2000, pp. 1540-1545.

Smela, Elisabeth, et al., "Electrochemically Driven Polypyrrole Bilayers for Moving and Positioning Bulk Micromachined Silicon Plates," *Journal of Microelectromechanical Systems*, vol. 8, No. 4, Dec. 1999, pp. 373-383.

Smela, Elisabeth, et al., "Thiol-Modified Pyrrole Monomers: 1. Synthesis, Characterization, and Polymerization of 1-(2-Thioethyl)pyrrole and 3-(2-Thioethyl)pyrrole," *Langmuir*, vol. 14, 1998, pp. 2970-2975.

Smela, Elisabeth, "Microfabrication of Ppy Microactuators and Other Conjugated Polymer Polymer Devices," *Journal of Micromechanics and Microengineering*, vol. 9, 1999, pp. 1-18.

Immerstrand, C., et al., "Conjugated-Polymer Micro- and Milliactuators for Biological Applications," *Materials research Society Bulletin*, Jun. 2002, pp. 1-4.

Madden, John D.W., et al., "Conducting Polymer Actuators as Engineering Materials," *Smart Structures and Materials 2002*, ed. Y. Bar-Cohen, SPIE Proceedings, vol. 4695, 2002, pp. 176-190.

Zhou, D., et al., "Actuators for the Cochlear Implant," *Synthetic Materials*, vol. 135-136, 2003, pp. 39-40.

http://www.micromuscle.com.

Brock, David L., Review of Artificial Muscle Based on Contractile Polymers. Massachusetts Institute of Technology Artificial Intelligence Laboratories. http://www.a1.mit.edu/projects/muscle/papers/memo1330/memo1330.html.

Material: Conducting polymers, Dielectric elastomers, Piezoelectric materials. http://www.designinsite.dk/htmsider.

Artificial Muscle Transducers. http://www.erg.sri.com/automation/actuators.html.

Miniature Electroactive-Polymer Rakes. http://www.nasatech.com/Briefs/Oct01/NPO20613.html.

Electroactive polymer. Nano Bioelectronics & Systems Research Center http://nanobio.snu.ac.kr/eng/research_5.html.

Polymers and Separations Research Lab (PolySep). Electroactive Polymers as Artificial Muscles—A Primer. http://polysep.ucla.edu/Research%20Advances/EAP/electroactive_polymers-asartifi.htm.

Aviation Research. You Decide. Electroactive Polymers 2: Ionic and Conductive Polymers. http://virtualskies.arc.nasa.gov/research/youDecide/ionicNConducPolym.html.

ElectroActive Polymers—EAPs. http://www.azom.com/details.asp?ArticleID=885.

http://www.darpa.mil/dso/trans/electropolymers/projects/EAP_Jan02_LJB.pdf.

* cited by examiner

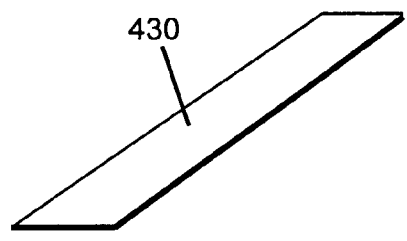
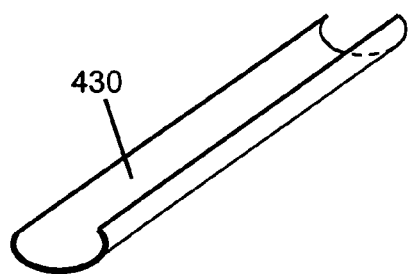
Fig. 14A                Fig. 14B
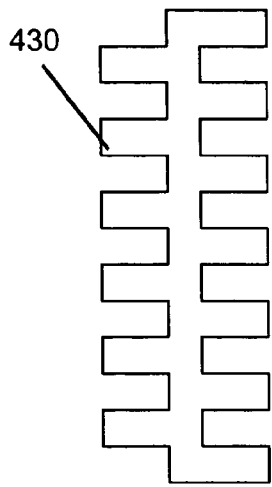
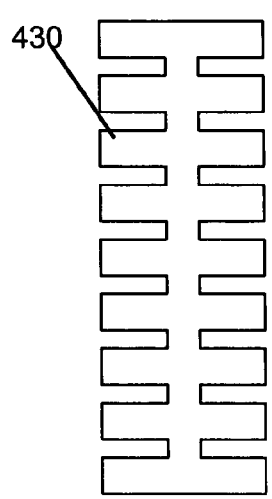
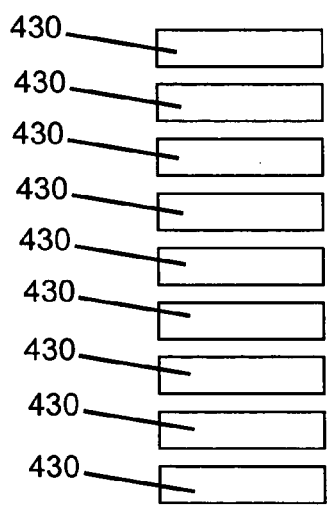
Fig. 15A                Fig. 15B                Fig. 15C

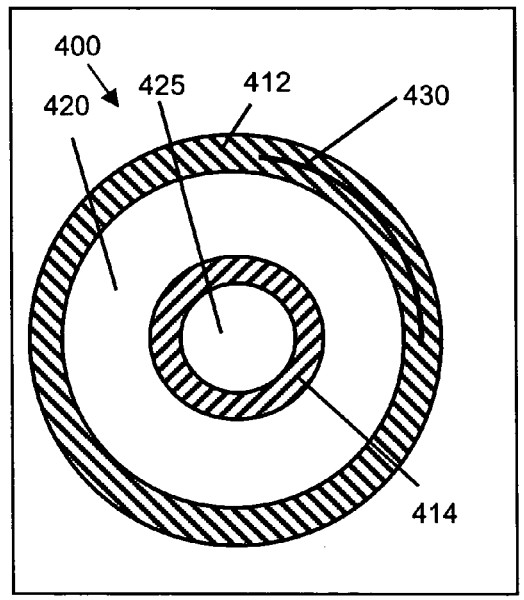 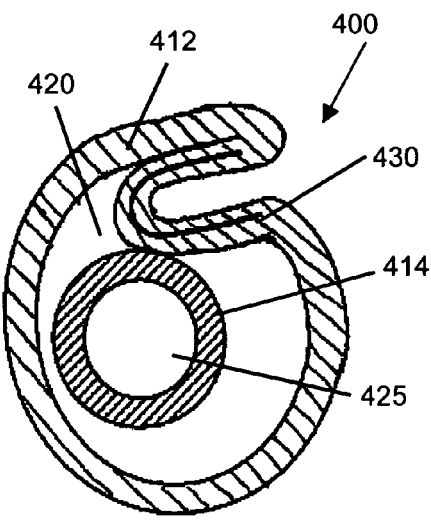
Fig. 16A
Fig. 16B
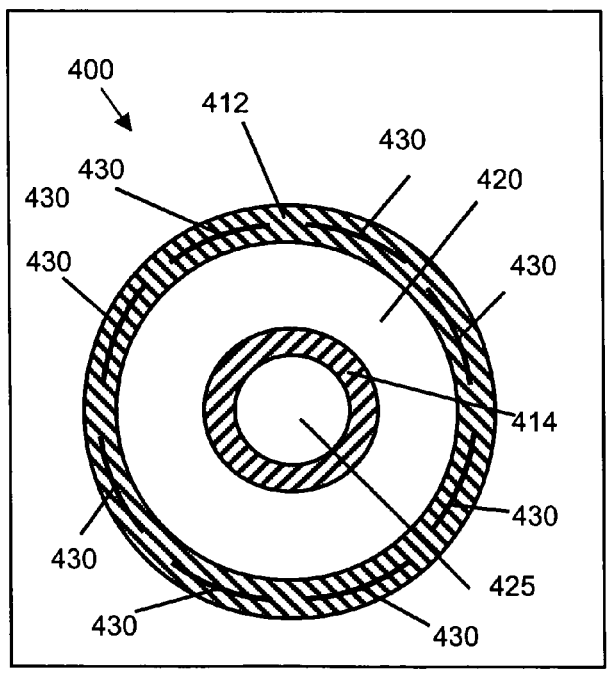 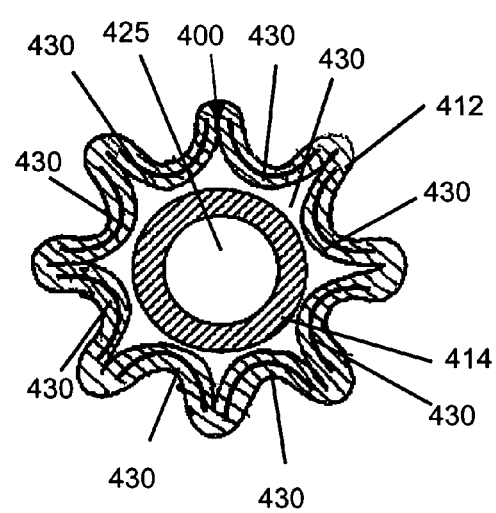
Fig. 17A
Fig. 17B

ELECTRICALLY ACTUATED MEDICAL DEVICES

FIELD OF THE INVENTION

This invention relates to medical devices for implantation or insertion into the body, and more particularly to medical devices such as catheters, guidewires, and aneurysm coils, in which electrically actuated materials, such as electroactive polymers and piezoelectric materials, are used to enhance or expand their functionality.

BACKGROUND OF THE INVENTION

Procedures are presently known for treatment of a variety of vascular conditions, including treatment of vascular obstructions and enlargements. For example, in a typical percutaneous transluminal coronary angioplasty (PTCA) procedure, a guide catheter is introduced into the cardiovascular system of a patient and advanced through the aorta until the distal end of the catheter is in the ostium of the designated coronary artery. Using fluoroscopy, a guidewire is then advanced through the guide catheter and across the site to be treated in the coronary artery. A balloon catheter is then advanced over the guidewire to the treatment site, and at which point the balloon is expanded to reopen the artery. To help prevent arterial closure, repair dissection, and/or prevent restenosis, a physician can implant an intravascular prosthesis, for example, a stent, inside the artery at the treatment site. Unfortunately, in some cases, the arterial obstruction is so extensive that the physician has difficulty advancing the various medical devices past the obstruction. Thus, there is, in general, a need to advance devices that have a cross-sectional profile that is as small as possible. Moreover, current balloon catheters can be described as having a hydraulic actuating mechanism. Because hydraulic systems are more efficient at larger dimensions, the present trend to downscale device sizes has created the need for actuators that efficiently function at very small diameters. Furthermore, in rare instances, the physician may have to withdraw a stent (or other prosthesis) that has tracked in an artery, during which time the edge of the stent may catch on a lesion or guiding catheter and be at risk for embolization.

In contrast to treating obstructions, other vascular procedures are used to treat vascular enlargements. For example, in one presently known method for the treatment of an aneurysm, the physician initially places a catheter into the mouth of the aneurysm. A coil is then inserted through the catheter and into the aneurysm. With some coils, for example, Guglilmi detachable coils (GDCs), if the physician does not like the coil's configuration, he or she can remove it and reposition it or choose another size coil. In the case of the GDC, the coil is a soft platinum coil that is soldered to a stainless steel delivery wire. When the coil is properly positioned within the aneurysm, a small current is applied to the delivery wire, dissolving the same at a position proximal to the platinum coil by means of electrolysis. Once electrolysis occurs, the delivery wire can be removed leaving the coil in place. Another coil can then be introduced. The process is continued until the aneurysm is densely packed with coils and no longer opacifies during diagnostic contrast injections. In general, the more tightly the coils are wound, the more densely the aneurysm is packed. There is a continuing need in the art for materials that will provide such coils.

SUMMARY OF THE INVENTION

The above-described and other challenges, needs and drawbacks of the prior art are addressed by the present invention.

According to a first aspect of the invention, a medical device is provided, which comprises the following: (a) an elongate body adapted for insertion into a body lumen of a patient (typically a mammalian subject, and more typically a human subject); and (b) an active region comprising a conductive polymer (for instance, polypyrrole), wherein the active region is disposed over the elongate body such that the medical device is expanded in at least one radial dimension (relative to the axis of the elongate body) upon volumetric expansion of the active region.

In some embodiments, the active region (or regions) directly expands the device in a radial direction. In other embodiments, the active region(s) indirectly expand the device by causing a passive deformable region to radially expand upon volumetric expansion of the active region.

The active region(s) of the device can be provided in a wide range of configurations. For example, an active region can surround the elongate body in the form of a circumferential band. As another example, an active region can be provided in the form of a longitudinal strip. As yet another example, an active region can be provided, which increases in radius as one travels in a distal-to-proximal direction, for example, gradually or in a step-wise fashion.

In some embodiments of the invention, the active region is disposed in a recess that is formed in the elongate body, for instance, in a circumferential recess or in a longitudinal recess.

In some embodiments, the active region is provided at a distal end of a catheter or guidewire, in which case the distal end may be flattened, for example, to improve the device's ability to negotiate body lumen obstructions. In some embodiments, the active region(s) are configured such that at least a portion of the length of the medical device is stiffened upon expansion of the active region(s). For example, this feature can be provided by circumferentially surrounding the elongate body with one or more active regions.

In some embodiments of the invention, the medical device comprises a cutting blade that is adapted to engage the tissue of a surrounding lumen after insertion of the device and expansion of the active region. Examples of cutting blades include metal cutting blades and diamond-tipped cutting blades. The cutting blade can be provided in a sheath, where desired.

According to another aspect of the invention, a medical device is provided that comprises: (a) an elongate body adapted for insertion into a body lumen; (b) a balloon; and (c) an active region comprising an electroactive polymer (for instance, polypyrrole), wherein the active region is adapted to radially advance at least a portion of the balloon when the balloon is in a substantially uninflated state.

In some embodiments of this aspect of the invention, the active region is adapted to radially advance at least the proximal portion of balloon; in others, at least the proximal and distal portions of the balloon are advanced; in still others, the proximal, central and distal portions of the balloon are advanced.

In some embodiments, at least a portion of the balloon is radially advanced by the direct volumetric expansion of the active region. In others, at least a portion of the balloon is radially advanced by a passive deformable region that radially expands upon the volumetric expansion of the active region.

In some embodiments, the medical device comprises a curvilinear member, and the active region is adapted to radially expand the curvilinear member. For example, the curvilinear member can be a spiral member, which can originate from and wrap around the elongate member of the catheter.

The spiral member can comprise, for example, an active layer disposed over a conductive layer, typically a metal.

According to another aspect of the invention, a medical device is provided (e.g., a balloon catheter, an arotic graft, a vena cava filter or a stent, such as a coronary vascular stent, peripheral vascular stent, a renal stent or a biliary stent, among many other devices), which comprises: (a) an insertable body adapted for insertion into a body lumen of a patient; (b) a device lumen within the insertable body; and (c) one or more electrically actuated members disposed along at least a portion of the length of the device lumen. The one or more electrically actuated members in this aspect of the invention are adapted to transform at least a portion of the length of the device lumen between an expanded state and a contracted state, in which state the insertable body is more readily inserted into the body lumen of the patient. In some embodiments, the one or more electrically actuated members extend along the entire length of the device lumen, while in others they extend along only a portion of the length (for instance, the insertable length) of the device lumen.

According to yet another aspect of the present invention, an aneurysm filler coil is provided which comprises: (a) an elongate conductive region (for instance, a metal such as gold or platinum); and (b) an active region comprising an electroactive polymer (for instance, polypyrrole). The active region and the conductive region are typically disposed relative to one another such that the device becomes more tightly coiled upon being disconnected from a source of electrical potential. In some embodiments, the active region is longitudinally disposed along the length of the elongate conductive region. For example, the active region can be disposed along one side of the conductive region, or it can form a spiral around the conductive region.

An advantage of the above aspects of the present invention is that medical devices can be provided, which have enhanced properties for advancement within body lumens, even in the face of near total obstructions.

Another advantage of the present invention is that medical devices can be provided in which hydraulic expansion mechanisms are replaced or supplemented, thereby allowing these devices to operate efficiently at very small diameters.

A further advantage of the present invention is that medical devices can be provided that have improved ability to retrieve stents or other prosthesis from a body lumen, with reduced risk of embolization.

Yet another advantage of the present invention is that aneurysm coils can be provided, which are able to coil more tightly upon being positioned within an aneurism.

Additional aspects, embodiments and advantages of the invention will become readily apparent to those of ordinary skill in the art upon review of the following detailed description in which several embodiments are set forth in detail.

BRIEF DESCRIPTION OF THE DRAWINGS

FIGS. 14A and 14B are schematic perspective views of the electrically actuatable member from the device of FIGS. 13A and 13B in uncurled and curled states, respectively, in accordance with an embodiment of the present invention.

FIGS. 15A and 15B are schematic top views of electrically actuatable members, in accordance with an embodiment of the present invention.

FIG. 15C is a schematic top view of a collection of electrically actuatable members, in accordance with an embodiment of the present invention.

FIGS. 16A and 16B are schematic, cross-sectional views of a balloon catheter shaft in expanded and contracted states, respectively, in accordance with an embodiment of the present invention.

FIGS. 17A and 17B are schematic, cross-sectional views of a balloon catheter shaft in expanded and contracted states, respectively, in accordance with another embodiment of the present invention.

DESCRIPTION OF THE SPECIFIC EMBODIMENTS

Figure 1A:
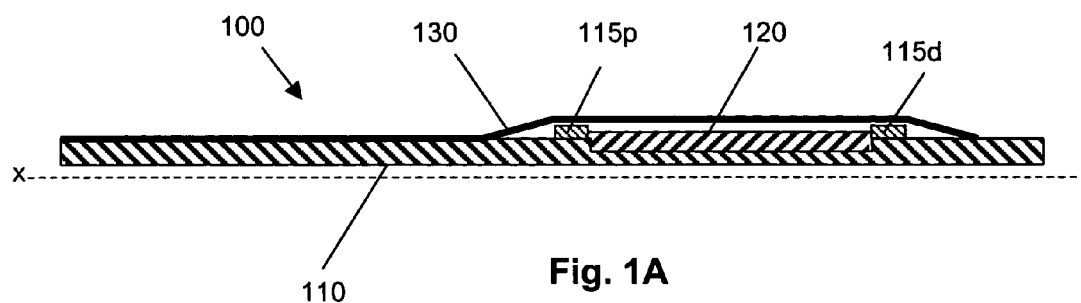
FIGS. 1A to 1C are schematic, partial (above axis only), longitudinal cross-sectional views of a catheter in accordance with an embodiment of the present invention.

The present invention now will be described more fully hereinafter with reference at times to accompanying drawings, in which specific embodiments of the present invention are shown. This invention may, however, be embodied in different forms and should not be construed as limited to the embodiments set forth herein.

In certain embodiments, the medical devices of the present invention are actuated, at least in part, using electroactive polymer (EAP) actuators. Electroactive polymers are polymers characterized by their ability to change shape in response to electrical stimulation.

The electroactive polymers that are typically used in connection with the present invention are ionic EAPs, more typically conductive EAPs that feature a conjugated backbone (e.g., they have a backbone that comprises and alternating series of single and double carbon-carbon bonds) and have the ability to increase electrical conductivity under oxidation or reduction. Some commonly known EAPs are polypyrroles, polyanilines, polythiophenes, polyethylenedioxythiophenes, poly(p-phenylene vinylene)s, polysulfones and polyacetylenes. Polypyrrole, which is one of the most stable of these polymers under physiological conditions, is pictured below:

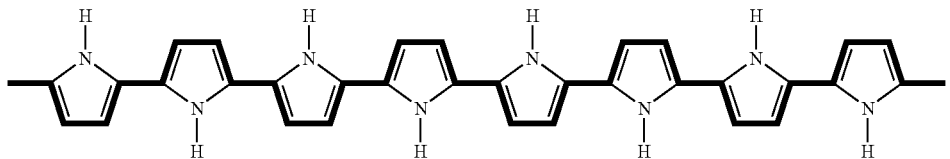

These EAPs are typically semi-conductors in their pure form. However, upon oxidation or reduction of the polymer, the electrical conductivity is understood to be changed from a semi-conductive regime to a semi-metallic regime. Such oxidation and reduction are believed to lead to a charge imbalance that, in turn, results in a flow of ions into or out of the material. These ions typically enter/exit the material from/into an ionically conductive electrolyte medium associated with the electroactive polymer.

It is well known that dimensional changes are effectuated in certain polymers by the mass transfer of the ions (which are surrounded by a shell of water molecules, commonly referred to as the "hydration shell") into or out of the polymer. For example, in some conductive polymers, expansion is believed to be due to ion insertion between chains, whereas in others inter-chain repulsion is believed to be the dominant effect. Regardless of the mechanism, the mass transfer of ions into and out of the material leads to an expansion or contraction of the polymer, delivering significant stresses (e.g., on the order of 1 MPa) and strains (e.g., on the order of 10%). These characteristics are ideal for construction of the devices of the present invention. As used herein, the expansion or the contraction of the active region of the device is generally referred to as "actuation."

Ionic EAPs also have a number of additional properties that make them attractive for use in the devices of the present invention, including the following: (a) they are lightweight, flexible, small and easily manufactured; (b) energy sources are available which are easy to control, and energy can be easily delivered to the EAPS; (c) small changes in potential (e.g., potential changes on the order of 1V) can be used to effect volume change in the EAPs; (d) they are relatively fast in actuation (e.g., full expansion/contraction in a few seconds); (e) EAP regions can be created using a variety of techniques, for example, electrodeposition; and (f) EAP regions can be patterned, for example, using photolithography, if desired.

The following elements are generally utilized to bring about electroactive polymer actuation: (a) a source of electrical potential, (b) an active region, which comprises the electroactive polymer, (c) a counter electrode and (d) an electrolyte in contact with both the active region and the counter electrode.

The electrolyte, which is in contact with at least a portion of the surface of the active region, allows for the flow of ions and thus acts as a source/sink for the ions. The electrolyte may be, for example, a liquid, a gel, or a solid, so long as ion movement is permitted. Where the electrolyte is a liquid, it may be, for example, an aqueous solution containing a salt, for example, an NaCl solution, a KCl solution, a sodium dodecylbenzene sulfonate solution, a phosphate buffered solution, physiological fluid, and so forth. Where the electrolyte is a gel, it may be, for example, a salt-containing agar gel or polymethylmethacrylate (PMMA) gel. Where the electrolyte is a solid, it may be, for example, a polymer electrolyte.

The counter electrode may be formed from any suitable electrical conductor, for example, a conducting polymer, a conducting gel, or a metal, such as stainless steel, gold or platinum. At least a portion of the surface of the counter electrode is generally in contact with the electrolyte, in order to provide a return path for charge.

As discussed above, the EAP-containing active region contracts or expands in response to the flow of ions out of, or into, the same. Essentially any electroactive polymer that exhibits contractile or expansile properties may be used in connection with the various active regions of the invention, including those listed above.

In accordance with certain embodiments of the invention, the active region is a polypyrrole-containing active region. Polypyrrole-containing active regions can be fabricated using a number of known techniques, for example, extrusion, casting, dip coating, spin coating, or electro-polymerization/deposition techniques. Polypyrrole-containing active regions can also be patterned, for example, using lithographic techniques, if desired.

As a specific example of a fabrication technique, polypyrrole can be galvanostatically deposited on a platinised substrate from a pyrrole monomer solution using the procedures described in D. Zhou et al., "Actuators for the Cochlear Implant," *Synthetic* Metals 135-136 (2003) 39-40. Polypyrrole can also be deposited on gold. In some embodiments, adhesion of the electrodeposited polypyrrole layer is enhanced by covering a metal such as gold with a chemisorbed layer of molecules that can be copolymerized into the polymer layer with chemical bonding. Thiol is one example of a head group for strong chemisorbtion to metal. The tail group should be chemically similar to the pyrrole monomer, so the use of a pyrrole ring attached to the thiol group (e.g., via a short alkyl chain) is a natural choice. Specific examples of such molecules are 1-(2-thioethyl)-pyrrole and 3-(2-thioethyl)-pyrrole. See, e.g., E. Smela et al., "Thiol Modified Pyrrole Monomers: 1. Synthesis, Characterization, and Polymerization of 1-(2-Thioethyl)-Pyrrole and 3-(2-Thioethyl)-Pyrrole," *Langmuir,* 14 (11), 2970-2975, 1998.

Various dopants can be used in the polypyrrole-containing active regions, including large immobile anions and large immobile cations. According to one specific embodiment, the active region comprises polypyrrole (PPy) doped with dodecylbenzene sulfonate (DBS) anions. When placed in contact with an electrolyte containing small mobile cations, for example, $Na^+$ cations, and when a current is passed between the polypyrrole-containing active region and a counter electrode, the cations are inserted/removed upon reduction/oxidation of the polymer, leading to expansion/contraction of the same. This process can be represented by the following equation:

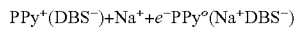

where $Na^+$ represents a sodium ion, $e^-$ represents an electron, $PPy^+$ represents the oxidized state of the polypyrrole, $PPy^o$ represents the reduced state of the polymer, and species are enclosed in parentheses to indicate that they are incorporated into the polymer. In this case the sodium ions are supplied by the electrolyte that is in contact with the electroactive polymer member. Specifically, when the EAP is oxidized, the positive charges on the backbone are at least partially compensated by the $DBS^-$ anions present within the polymer. Upon reduction of the polymer, however, the immobile $DBS^-$ ions cannot exit the polymer to maintain charge neutrality, so the smaller, more mobile, $Na^+$ ions enter the polymer, expanding the volume of the same. Upon re-oxidation, the $Na^+$ ions again exit the polymer into the electrolyte, reducing the volume of the polymer. The source of electrical potential for use in connection with the present invention can be quite simple, consisting, for example, of a dc battery and an on/off switch. Alternatively, more complex systems can be utilized. For example, an electrical link can be established with a microprocessor, allowing a complex set of control signals to be sent to the EAP-containing active region(s).

EAP-containing active regions can be provided that either expand or contract when an applied voltage of appropriate value is interrupted depending, for example, upon the selection of the EAP, dopant, and electrolyte.

Additional information regarding EAP actuators, their design considerations, and the materials and components that may be employed therein, can be found, for example, in E. W. H. Jager, E. Smela, O. Inganas, "Microfabricating Conjugated Polymer Actuators," *Science,* 290, 1540-1545, 2000; E. Smela, M. Kallenbach, and J. Holdenried, "Electrochemically Driven Polypyrrole Bilayers for Moving and Positioning Bulk Micromachined Silicon Plates," *J. Microelectromechanical Systems,* 8(4), 373-383, 1999; U.S. Pat. No. 6,249,076, assigned to Massachusetts Institute of Technology, and *Proceedings of the SPIE,* Vol. 4329 (2001) entitled "Smart Structures and Materials 2001: Electroactive Polymer and Actuator Devices (see, e.g., Madden et al, "Polypyrrole actuators: modeling and performance," at pp. 72-83), each of which is hereby incorporated by reference in its entirety.

In certain other embodiments, the medical devices of the present invention are actuated, at least in part, using materials involving piezoelectric, electrostrictive, and/or Maxwell stresses.

According to an aspect of the present invention, medical devices are provided that comprise an elongate body, which is adapted for insertion into a body lumen. An active region that comprises a conductive polymer is disposed over the elongate body such that the medical device is expanded in at least one radial dimension (i.e., in at least one dimension that is orthogonal to the longitudinal axis of the device) upon volumetric expansion of the active region.

For example, FIG. 1A is a schematic illustration of a balloon catheter 100, which can be used, for example, to expand a stent (not illustrated) at a site of arterial obstruction. In the embodiment shown, distal portions of the catheter 100 are to the right, while proximal portions are to the left. The axis of the catheter (which also corresponds to the axis of the body lumen, e.g., artery, into which the catheter is inserted) is designated by the letter "x". Proximal and distal markers (e.g., radiographic markers), 115p, 115d, are provided within the catheter as is known in the art, to assist in placing the catheter at an appropriate position within the body lumen.

The balloon catheter includes an inner lumen 110 (or a shaft, as the case may be) and a balloon 130. Although not shown, if desired, the balloon 130 can be provided with cutting blades, as is known in the art. Disposed between the inner lumen 110 and the balloon 130 is an active region 120, which contains an electroactive polymer. The active region 120 can be provided in various configurations. For example, in the embodiment illustrated in FIG. 1A, the active region 120 is provided in a band around the inner lumen 110. However, multiple actuators in various configurations (for example, a series of longitudinal strips, a series of circumferential bands, a series patches, and so forth) can also be employed to achieve a similar result.

In the embodiment illustrated, the active region 120 is provided in a recess formed in the inner lumen 110. Although this is not required, by providing the active region 120 within a recess, an increase in the inserted profile of the device will be minimized, if not avoided entirely.

If desired, a contact electrode (not shown), for example, one formed of gold (Au), can be provided between the inner lumen 110 and the active region 120, to actuate the active region 120. For instance, in some embodiments, the inner lumen 110 is not formed of a conductive material and therefore cannot function as an electrode.

The counter electrode function can be performed, for example, by a separate dedicated conductive member (not shown) within the device 100. Alternatively, a conductive element of the device 100 itself can be used for this purpose. In any case, care is generally taken to avoid electrically shorting the active region (or its electrode) with the counter electrode.

An electrolyte (not separately illustrated) can be provided, for example, within a sealed structure that also encloses the active region and counter electrode. If desired, the balloon 130 can serve this function. In other embodiments, physiological fluid can serve as the electrolyte.

Figure 1B:
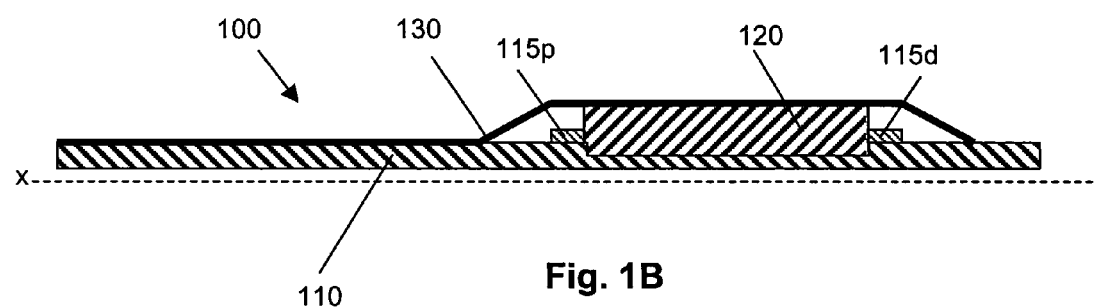

Taking as an example the specific embodiment where a PPy-containing active region 120 is employed over a gold or platinum electrode contact within the catheter 100, the device will operate as follows: When a positive potential is applied to the gold electrode contact, electrons are removed from the PPy, and it is oxidized from its neutral state ($PPy^o$) to its oxidized state ($PPy^+$). This is a reversible process. Thus, the PPy can be reduced from its oxidized state back to its neutral state by adding electrons. In this example it is further assumed that the PPy is doped with $DBS^-$ (dodecylbenzenesulfonate) anions and the device is operated in an electrolyte solution, for example, an NaDBS solution. During reduction of the polypyrrole containing region, small cations, in our case $Na^+$ (surrounded a hydration shell), are inserted into the active region to achieve charge neutrality in the polypyrrole containing active region 120. This swells the active region 120, pushing the balloon 130 radially outward as illustrated in FIG. 1B. This also exerts straightening and stiffening forces on the inner lumen 110. The expansion of the active region 120 also acts to center the balloon and fix it longitudinally in the body lumen.

Figure 1C:
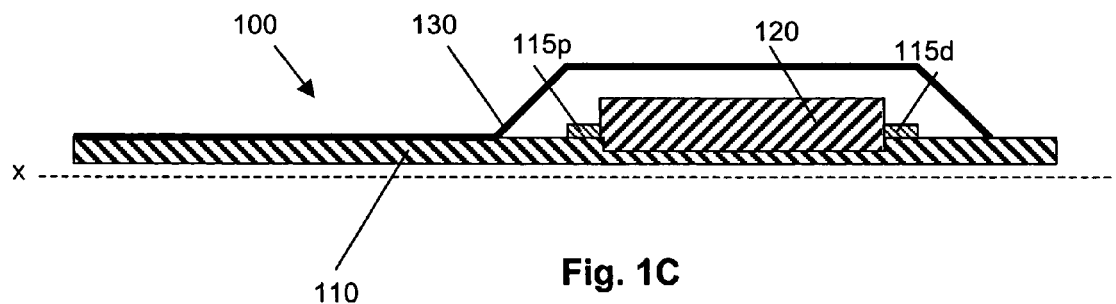

Note that the EAP-containing active region 120 radially expands the balloon (and any associated prosthesis, such as a stent) outward from a fully crimped state. As the balloon's diameter is increased, the balloon enters into a more efficient operating range, where less pressure is required to generate the large strains that are afforded by hydraulic actuation of this type. The balloon is then expanded as illustrated in FIG. 1C. Hence, in this embodiment, the first actuator (i.e., the EAP-containing active region 120) improves the efficiency of the second actuator (i.e., the balloon 130).

After expansion, the balloon is deflated, and the above-described process is reversed (i.e., the PPy is oxidized, expelling the Na$^+$ ions from the active region 120 and shrinking the same). Once in this state, the device 100 is withdrawn from the body lumen, completing the procedure.

For the PPy/DBS active region described above, the neutral (expanded) state is achieved at an applied voltage of about V=−1 V (vs. an Ag/AgCl reference electrode) and the oxidized (contracted) state is achieved at V=0 V.

FIG. 2S illustrates a balloon catheter 100 in accordance with another embodiment of the invention. The balloon catheter 100 of FIG. 2S, like that of FIG. 1A, includes an inner lumen/shaft 110 and a balloon 130. However, unlike that of FIG. 1A, the balloon catheter 100 of FIG. 2S does not contain proximal and distal markers that are distinct from the active region. Instead, the balloon catheter 100 of FIG. 2S contains active regions 120a and 120b, which are positioned beneath the balloon 130 near the proximal and distal ends of the same. These active regions 120a and 120b (e.g., active regions comprising polypyrrole) are deposited onto metal regions 123a and 123b (e.g., gold or platinum bands) using techniques such as those discussed above. In addition to being conductive, the metal regions 123a and 123b are also radio-opaque, allowing them to serve as proximal and distal radiographic markers.

Figure 2A:
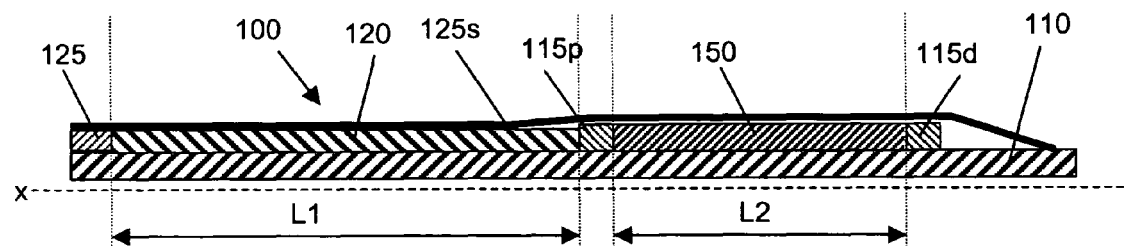
FIGS. 2A and 2B are schematic, partial, longitudinal cross-sectional views of a catheter in accordance with another embodiment of the present invention.

In the devices of FIG. 1A and FIG. 2S, the expanding EAP-containing active region directly exerts pressure on the balloon. In other embodiments of the present invention, however, the expanding EAP-containing active region exerts pressure upon a passive material, which, in turn, radially expands the balloon. FIG. 2A, for example, illustrates a balloon catheter 100, which like FIG. 1A, includes an inner lumen 110, proximal and distal markers 115p, 115d, active region 120, and balloon 130. However, the device of FIG. 2A further includes a fixed member 125 and an elastic passive member 150, which can be, for example, a member formed from rubber or a rubber-like elastic material.

Figure 2B:
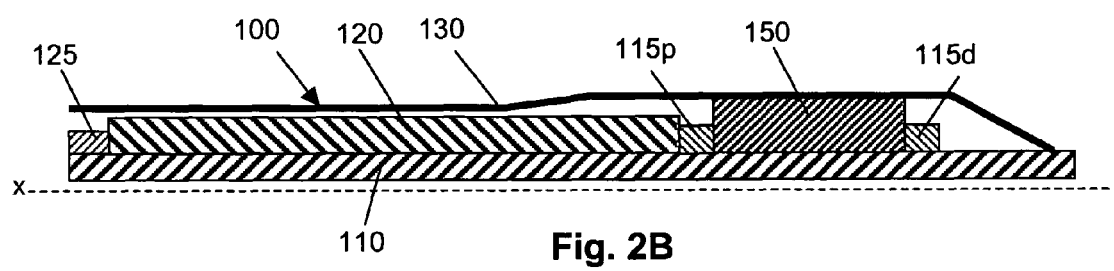

Comparing FIG. 2A with FIG. 2B, it can be seen that upon expansion of the active region 120, the proximal marker 115p (which is slidable along lumen 110 in this embodiment) is forced to the right, compressing passive member 150 against the distal marker 115d (which is fixed in this embodiment). Being constrained in this fashion, the passive member 150 radially expands to engage the balloon 130, with the attendant advantages discussed above in connection with FIGS. 1A-1C. In contrast to the device of FIGS. 1A-1C, which provides high stress but low strain, the embodiment of FIGS. 2A-2B can provide the reverse, if the ratio L1/L2 is large enough.

Figure 3A:
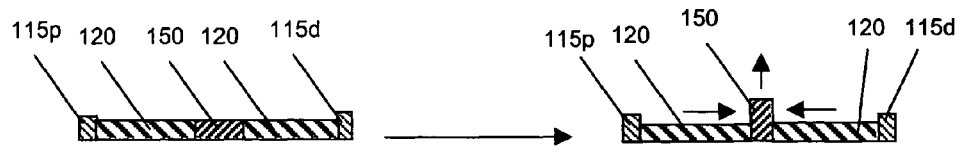
FIGS. 3A and 3B are schematic, partial cross-sectional views illustrating radial expansion via passive members, in accordance with two embodiments of the present invention.
Figure 3B:

Additional mechanisms of this type are shown in FIGS. 3A and 3B, which illustrate fixed proximal and distal markers 115p, 115d, active regions 120 and passive members 150. In FIG. 3A, the active regions 120 compress the passive member 150 from both the distal and proximal ends of the device, radially expanding the passive member 150. In FIG. 3B, a central active region 120 compresses proximal and distal passive members 150, radially expanding the same.

Figure 4A:
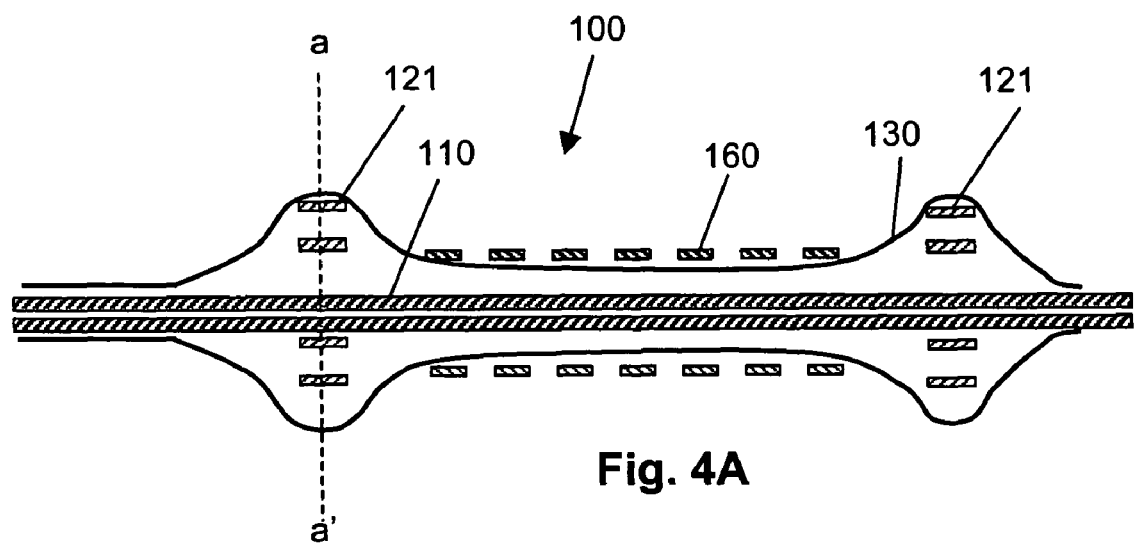
FIG. 4A is a schematic, partial, longitudinal cross-sectional view of a catheter in accordance with another embodiment of the present invention.
Figure 4B:
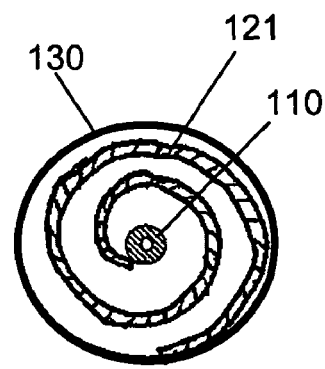
FIG. 4B is a schematic, radial cross-sectional view of the catheter of FIG. 4A, taken at the position indicated by line a-a' in FIG. 4A.

Another embodiment of the invention is illustrated in FIG. 4A, which shows a schematic longitudinal cross-sectional view of the distal portion of a balloon catheter 100, and in FIG. 4B, which shows a schematic radial cross-sectional view of the balloon catheter 100 of FIG. 4A, taken at the position of line a-a'. Balloon catheter 100 includes an inner lumen 110 (or shaft) and a balloon 130. A stent 160 is positioned over the balloon 130. Beneath the balloon 130 are two EAP-containing actuators 121, which are provided in the shape of a planar coil, as seen more clearly in FIG. 4B. The EAP-containing actuators 121 are illustrated in their expanded state. The EAP-containing actuators 121 can comprise, for example, a gold or platinum base onto which a polypyrrole-containing active layer is deposited. An electrolyte and counter electrode (not shown) can be provided, for example, as previously discussed. Depending upon whether the active layer is deposited on the outside or the inside of the coil, the coil will either tighten (and thus radially contract) or loosen (and thus radially expand) upon expansion of the active layer, and vice versa.

As previously noted, in rare instances, a physician may be forced to withdraw a stent (or other prosthesis) that has tracked in an artery, during which time the edge of the stent may catch at risk of embolization. However, by providing the catheter 100 with EAP-containing actuators 121, for example, at the proximal end, at the distal end, or at both (as illustrated), the balloon 130 can be pushed beyond the radius of the stent 160 to reduce this risk.

Figure 5A:
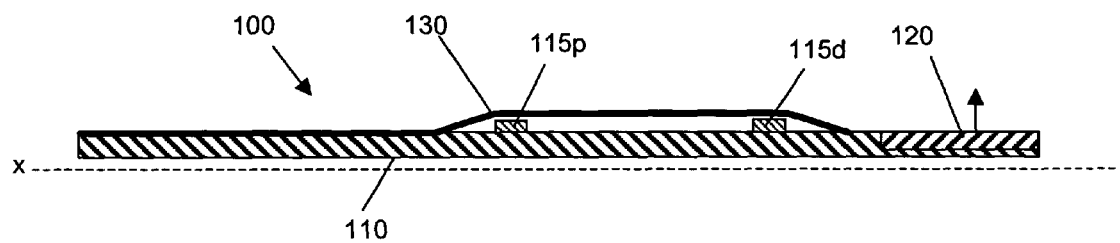
FIGS. 5A and 5B are schematic, partial, longitudinal cross-sectional views of a catheter in accordance with another embodiment of the present invention.
Figure 5B:
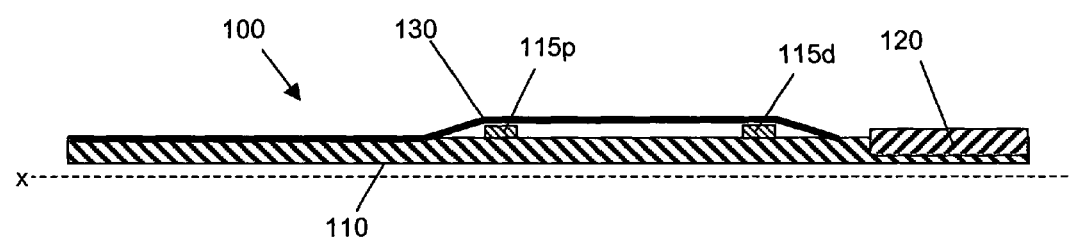

Yet another embodiment of the invention is illustrated in FIG. 5A. Like that of FIG. 1A, the catheter apparatus 100 of FIG. 5A includes an inner lumen 110 (or shaft), proximal and distal markers 115p, 115d, and a balloon 130. However, unlike the embodiment illustrated in FIG. 1A, the active region 120 is provided at the distal tip of the catheter apparatus 100, rather than beneath the balloon 130. FIG. 5B illustrates the device of FIG. 5A upon expansion of the EAP-containing active region 120.

By providing the active region 120 at the distal tip, this device 100 can be used, for example, to widen vascular obstructions, allowing the device 100 to be properly positioned relative to the obstruction. In certain embodiments, the surrounding physiological fluid (not illustrated) is used as a source/sink for the small ions which enter/exit the active region 120 during oxidation/reduction of the electroactive polymer. A counter electrode (not illustrated) is also typically contacted with the physiological fluid in these embodiments, completing the current path. For example, a guidewire (not illustrated) extending through the inner lumen 110 can be used for this purpose, so long as care is taken to prevent electrical shorting as discussed above.

Figure 6:
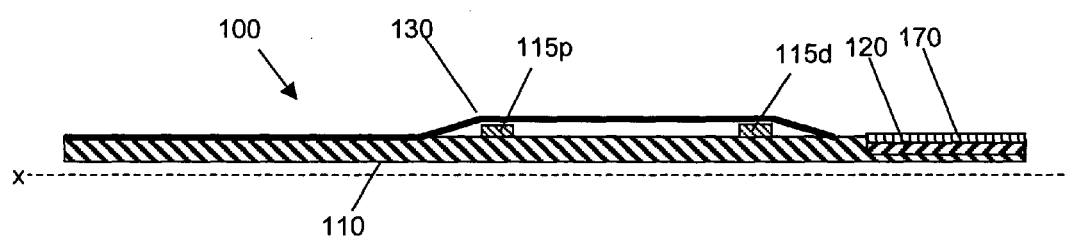
FIGS. 6-8 are schematic, partial, longitudinal cross-sectional views of catheters in accordance with various additional embodiments of the present invention.

FIG. 6 illustrates another embodiment of the invention, which is substantially like that of FIG. 5A, except that cutting blades 170 (one illustrated) are provided on the outside circumference of the active region 120. The cutting blades can be formed from a variety of materials, including metallic blades, for example, stainless steel blades, and diamond tipped blades (diamond blades are discussed, for example, in Ser. No. 10/212,508 entitled "Tubular cutting process and system"). Although the blade illustrated extends longitudinally, a variety of configurations are possible, including various configurations known in the cutting balloon art, such as segmented, notched and spiral configurations. If desired, the cutting blades can be retracted into a protective sheath prior to use. Alternatively the blades can be sheathed within a soft deformable or flowable polymer. Upon expansion of the active region, the deformable or flowable polymer is compressed, allowing the blades to engage adjacent tissue.

Figure 7:
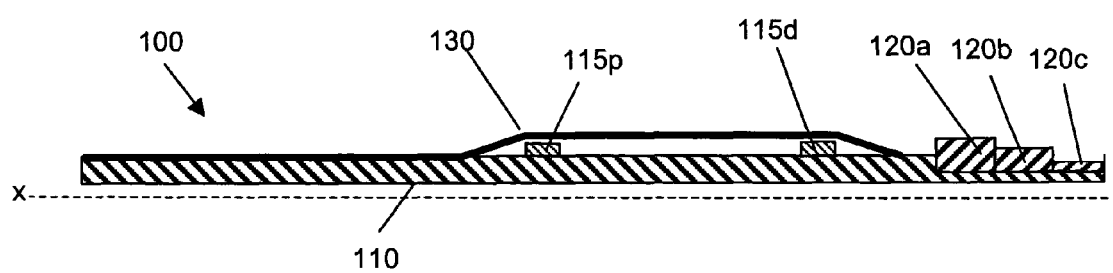
Figure 8:
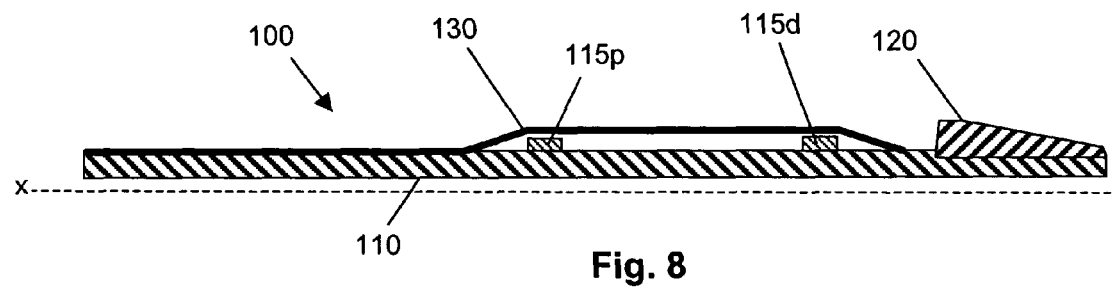

Although a single active region 120 is provided in a band around the inner lumen 110 in FIGS. 5A, 5B and 6, a number of active regions, for example, a series of longitudinal strips, a series of bands, and so forth, can also be employed to achieve a similar result. Moreover, the catheter 100 can be provided with a series active regions 120a, 120b, 120c, which are of progressively larger outer radius (i.e., they are disposed in a telescoping or stepped arrangement) as one proceeds proximally from the distal tip of the catheter as illustrated in FIG. 7. Alternatively, a similar effect can be achieved by utilizing an active region 120 of gradually increasing outer radius as illustrated in FIG. 8. Although not illustrated, the underlying lumen 110 can also be stepped or graded in this fashion.

In still other embodiments, apparatus like those described in connection with FIGS. 5A, 5B, 6, 7 and 8 are provided, but without a balloon and/or with a central solid shaft, rather than a lumen.

Figure 20A:
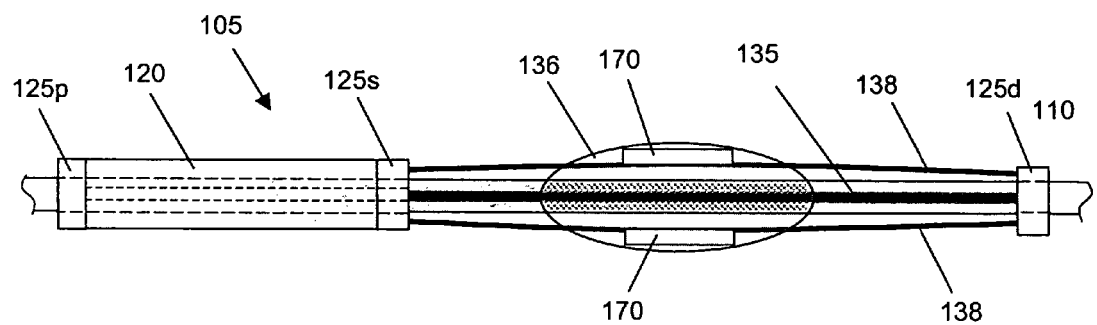
FIGS. 20A and 20B are schematic, partial, longitudinal views of an assembly that is adapted to radially expand a plurality of cutting blades, in accordance with an embodiment of the present invention.
Figure 20B:
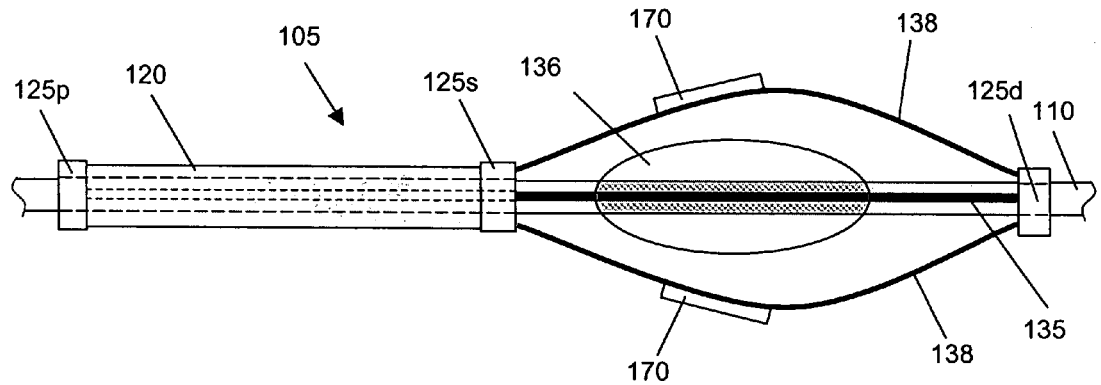

In contrast to the embodiment of FIG. 6, the cutting blades 170 in the embodiments illustrated in FIGS. 20A and 20B are attached to a passive, rather than active, member. FIGS. 20A and 20B illustrate an assembly 105, which is slidable over an inner lumen (or a solid shaft such as a guidewire) 110. The assembly 100 includes a proximal ring 125p and a distal ring 125d, which are axially spaced at a fixed distance from one another by stiff elongated structural member 135 (e.g., a rigid strip or a rod). An active region 120 is disposed between the proximal ring 125p and slidable ring 125s, whose distance from the proximal ring 125p (and the distal ring 125d) is not fixed. The assembly 105 further includes deformable members such as flexible members 138 (e.g., flexible wires), which are attached at the proximal end to ring 125s and at the distal end to distal ring 125d. Cutting blades 170 are attached to outer surfaces of flexible members 138. (Note that although the blades 170 are illustrated as separate from the flexible members 138 in this embodiment, one can grind the flexible members 138 themselves to have a sharp face, if desired.) Cutting blades 170 and a portion of flexible members 138 are disposed in depressions (e.g., slits, not shown) within a polymer body 136 (e.g., a polymer ball, which as illustrated is partially transparent).

As seen by comparing FIG. 20A with FIG. 20B, upon expansion of the active region 120, the slidable ring 125s is pushed toward the distal end of the device, relative to proximal and distal rings 125p, 125d. Consequently, the flexible members 138, which are disposed between slidable ring 125s and the distal ring 125d, are pushed out through the slits in the protective polymer ball 136, along with the cutting blades 170 attached thereto. Sliding the assembly 105 in actuated form will slice through surrounding tissue, such as an artery wall.

Figure 21A:
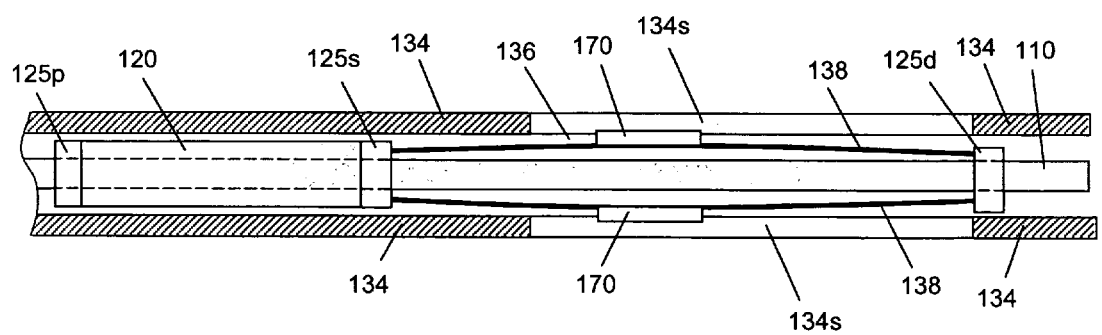
FIGS. 21A and 21B are schematic, partial, longitudinal views of an assembly that is adapted to radially expand a plurality of cutting blades, in accordance with another embodiment of the present invention.
Figure 21B:
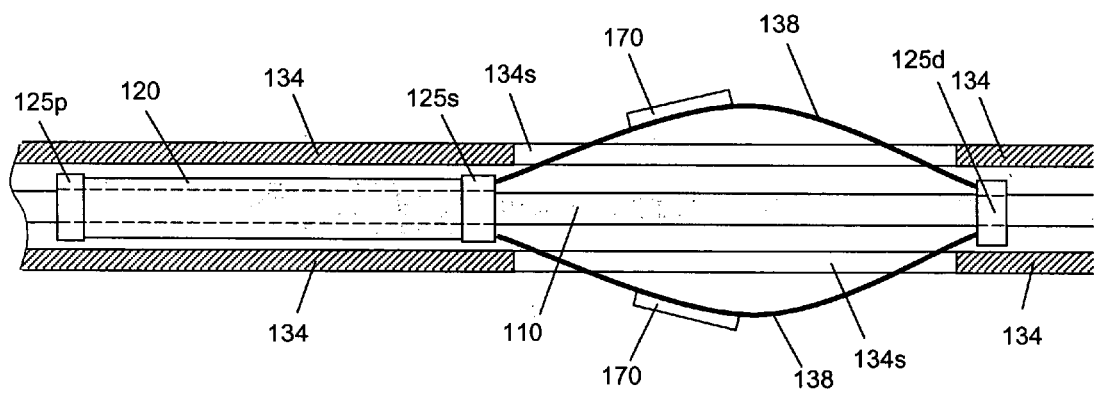

Another embodiment of the invention is illustrated in FIGS. 21A and 21B. The mechanism of engagement of the cutting knives 170 in this embodiment is similar to that of FIGS. 20A-20B, with the active region 120 pushing a slidable ring 125s toward the distal end of the device, resulting in the outward movement of flexible members 138. However, unlike FIGS. 20A-20B, rather than emerging from slits formed in a polymer ball 136, the knives 170 emerge from slots 134s that are formed in a surrounding catheter tube 134, which is illustrated in cross-section in FIGS. 21A and 21B. Furthermore, proximal and distal rings 125p, 125d are axially spaced apart by a structural member 135 in FIGS. 20A-20B. In contrast, in FIGS. 21A and 21B, the distal and proximal rings 125d and 125p are not movable relative to the member 110 (e.g., a core wire), but are rather fixed to the member 110, eliminating the need for a structural member 135 to keep the rings 125d, 125p axially spaced apart. The flexible members 138 are fixed to the central core wire 110 via the distal ring 125d, while the active member 120 is fixed to the core wire 110 via the proximal ring 125p.

Cutting blades can be deployed from guidewires, such as those to follow, using schemes analogous to those described above.

Figure 9A:
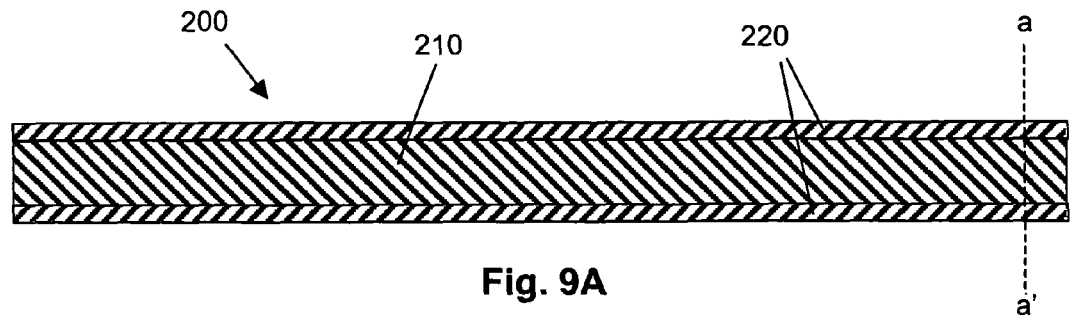
FIG. 9A is a schematic, partial, longitudinal cross-sectional view of a guidewire in accordance with an embodiment of the present invention.

Turning now to FIG. 9A, a composite guidewire 200 is illustrated therein, which comprises a guidewire core 210 having an active coating 220. The guidewire core 210 can be any of a variety of guidewire structures known in the art. The active coating 220 provided over the guidewire core 210, comprises an electroactive polymer, for example, a polypyrrole polymer as described above. A gold or platinum layer (not shown) is deposited on the guidewire core 210, in this particular embodiment to act as an electrode contact for the overlying active coating 220. As above, an electrolyte can be provided within a self-contained structure, or the surrounding physiological fluid can be used as a source/sink for the ions which enter/exit the active coating during operation.

By placing the active coating 220 over the entirety of the guidewire core 210 (or only over selected portions thereof), and by applying an appropriate potential, the thickness as well as the stiffness of the composite guidewire 200 can be varied. Increasing the thickness of the guidewire 200 is useful for expanding obstructions as previously discussed. Increasing the stiffness of the guidewire 200 will improve the practitioner's ability to push the guidewire through obstructions. Because the stiffness of this type of structure is predicted to change with the fourth power of the outer dimension, any change in the outer layer thickness should have a significant effect on stiffness.

Figure 9B:
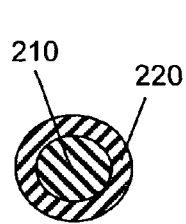
FIG. 9B is a schematic, radial cross-sectional view of the guidewire of FIG. 9A, taken at a position indicated by line a-a' in FIG. 9A.
Figure 10A:
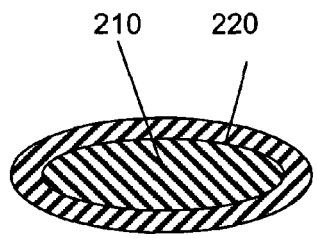
FIGS. 10A and 10B are schematic, radial cross-sectional views of the guidewire of FIG. 9A, taken at a position indicated by line a-a' in FIG. 9A, in accordance with two alternate embodiments of the present invention.
Figure 10B:
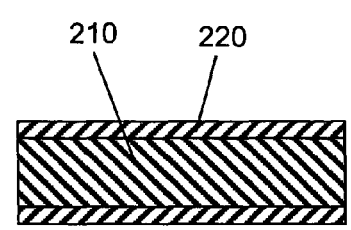

FIG. 9B is a schematic cross-sectional view taken across the guidewire 200 at the position indicated by line a-a' in FIG. 9A, and illustrates a cylindrical guidewire core 210 with an annular active coating 220 of even thickness. In additional embodiments, however, the guidewire core 210 is flattened, for example, as illustrated in the radial cross-sections of FIGS. 10A and 10B. Guidewires with flattened tips are described, for example, in U.S. Pat. No. 4,830,023 to de Toledo et al. By flattening at least the tip of the guidewire 200, the ability to penetrate obstructions is improved. Moreover, the guidewire core 210 need not be completely surrounded by the active coating 220, as illustrated in FIG. 10B.

In additional embodiments, the ability to penetrate and expand obstructions is further improved by providing the guidewire with stepped or graded regions like those described above in connection with FIGS. 7 and 8.

Figure 11A:
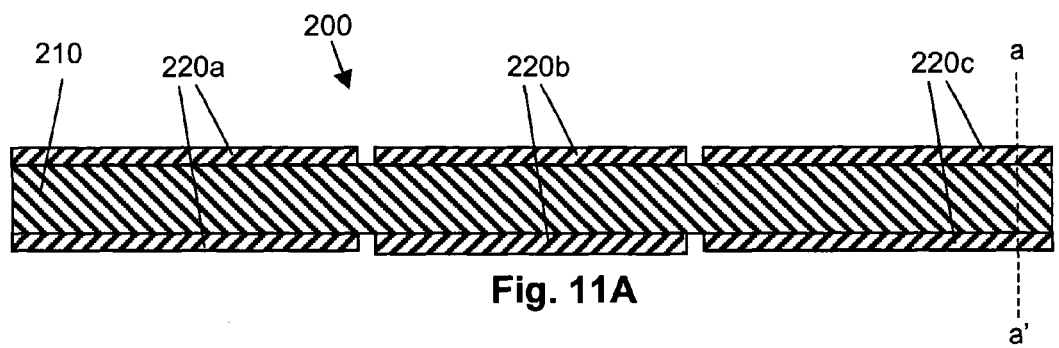
FIG. 11A is a schematic, partial, longitudinal cross-sectional view of a guidewire in accordance with another embodiment of the present invention.
Figure 11B:
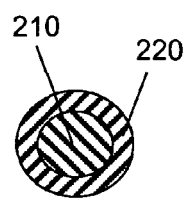
FIG. 11B is a schematic, radial cross-sectional view of the guidewire of FIG. 11A, taken at a position indicated by line a-a' in FIG. 11A.

An active coating 220 like that described in FIGS. 9A and 9B above can be provided, for example, over the entire guidewire core 210, over only a distal portion (e.g., the tip) of the guidewire core 210, and so forth. Moreover, a number of active coating regions 220 can be utilized, for example, as a series of longitudinal strips (not illustrated) or a series of circumferential bands as illustrated in FIGS. 11A and 11B. These active coating regions 220a, 220b, 220c can be operated as a group, or they can be operated individually by providing independent electrical connections to each, thereby allowing the degree of stiffness and expansion of the guidewire 200 to be varied along its length.

Figure 22A:
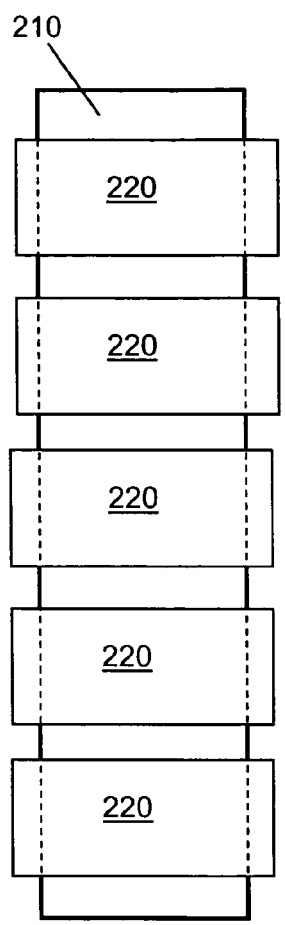
FIGS. 22A-22C, 23A-B and 24A-B are schematic, partial longitudinal views of lumens or shafts, in accordance with various embodiments of the present invention.
Figure 22B:
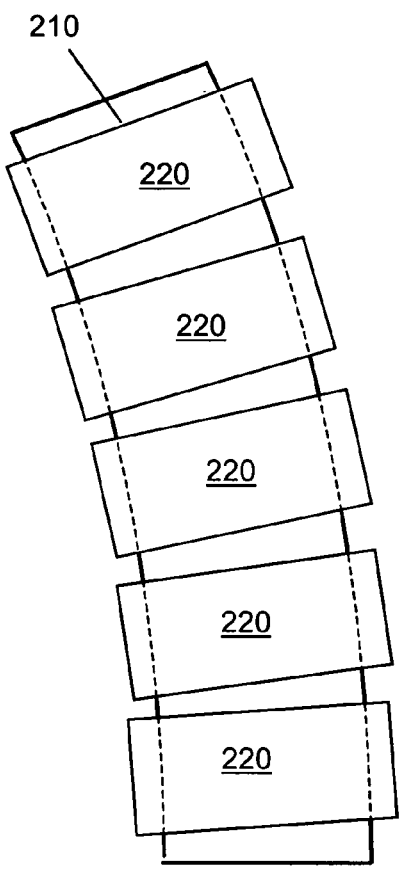
Figure 22C:
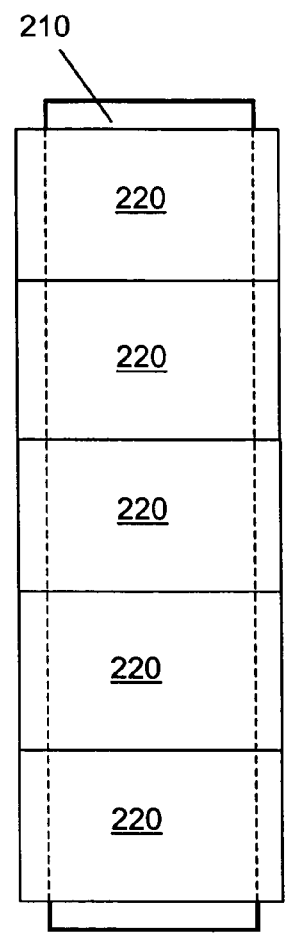

In other embodiments, the stiffness of an underlying member (e.g., a guide wire) is varied based on longitudinal expansion, rather than (or in addition to) radial expansion. For example, FIG. 22A illustrates a series active member rings 220 spaced along a lumen or shaft 210. As illustrated in FIG. 22B, the spacing between the rings allows the lumen/shaft 210 to bend readily. However, as illustrated in FIG. 22C, upon longitudinal expansion of the rings 220, the gaps between the rings 220 are reduced (or eliminated) thereby constraining the degree to which the lumen/shaft 210 can be bent without encountering resistance due to the rings 220 contacting one another.

Figure 23A:
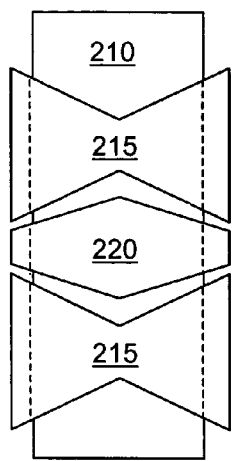
Figure 23B:
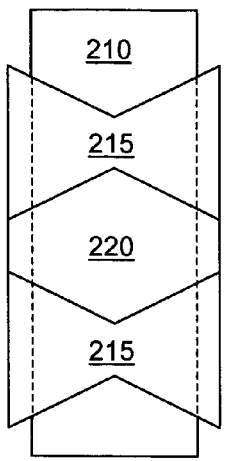

In other embodiments, the active rings engage regions of another material (e.g., a stiff material such as a metal or hard plastic). For example, FIG. 23A illustrates an active ring 220 and two stiff material rings 215 spaced along a lumen or shaft 210. Analogous to FIGS. 22A-C above, the spacing between the active ring 220 and the stiff material rings 215 in FIG. 23A allows the lumen/shaft 210 to bend readily. Upon expansion of the active ring 220 as illustrated in FIG. 23B, however, bending is restricted.

Figure 13A:
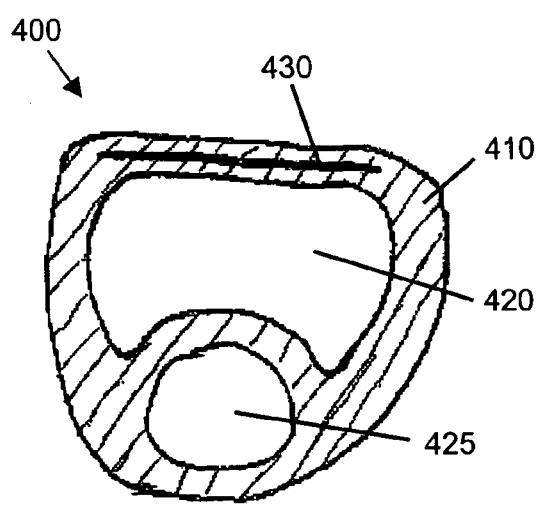
FIGS. 13A and 13B are schematic, cross-sectional views of a balloon catheter shaft in expanded and contracted states, respectively, in accordance with an embodiment of the present invention.
Figure 13B:
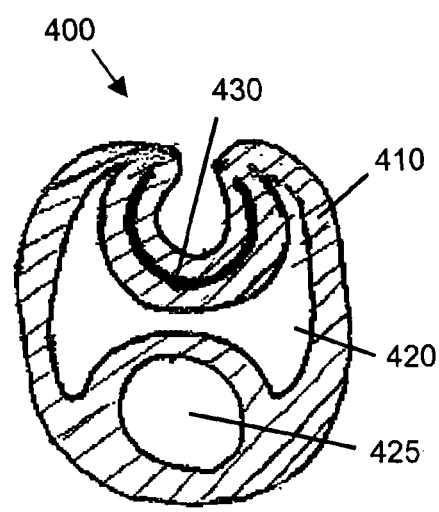
Figure 24A:
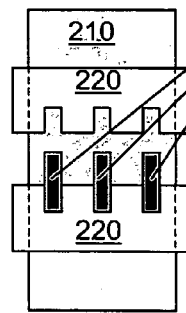
Figure 24B:
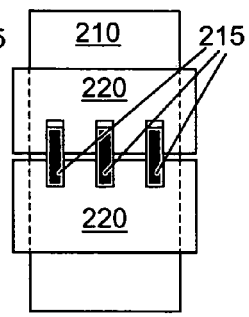
Figure 25:
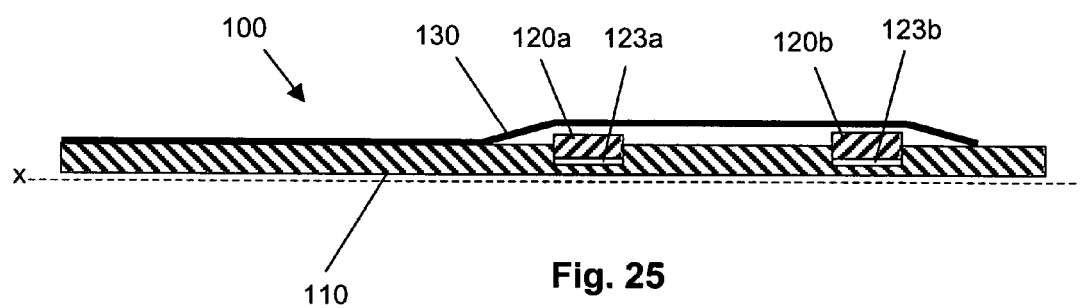
FIG. 25 is a schematic, partial, longitudinal, cross-sectional view of a catheter in accordance with yet another embodiment of the present invention.

As another example, FIG. 24A illustrates two active rings 220a, 220b spaced along a lumen or shaft 210. Three pins 215 formed from a stiff material are embedded in one active ring 220a, while slots for receiving the pins 215 are formed in the other active ring 220b. The lumen/shaft 210 is allowed to bend readily when the active ring 220a, 220b is in the contracted state as illustrated in FIG. 24A. However, upon expansion of the active rings 220a, 220b as illustrated in FIG. 24B, the pins 215 embedded active ring 220a engage the slots in active ring 220b, restricting bending. In other embodiments, only one of the rings 220a, 220b is an active ring, while the other ring is formed from a rigid material. Other aspects of the present invention are directed to medical devices having expandable and contractible lumens. An embodiment of this aspect of the present invention is illustrated in FIGS. 13A and 13B, which contain cross-sectional views of a shaft for a balloon catheter 400 in expanded and contracted states, respectively. The balloon catheter shaft 400 includes an elongate body 410, which is provided with two lumens in this particular embodiment, a guidewire lumen 425 and an inflation lumen 420. The elongate body 410 is fabricated, for example, from a polymeric or other flexible material, via extrusion or another commercially suitable process known in the art. The balloon catheter shaft 400 further comprises an electrically actuated member 430, which is in this embodiment is in the form of an elongated strip that is disposed within an outer wall of the elongate body 410.

Electrically actuated members 430 for use in conjunction with this aspect of the present invention include those constructed from electroactive polymers and from other materials which involve piezoelectric, electrostrictive or Maxwell stresses. Electroactive polymer actuators are discussed elsewhere herein. Piezoelectric and electrostrictive materials are materials that mechanically deform upon application of an external electric field and, conversely, that generate an electric charge when they are mechanically deformed. Such actuators may be structures of composite materials, layers of different materials (e.g., metal-insulator-metal structures) and innumerable other combinations. A few specific examples of piezoelectric materials include ceramic materials such as Lead Zirkonate Titanate PZT-5, Lead Titanate PT, Lead Metaniobate $PbNb_2O_6$, barium titanate and quartz, among others; metallic piezoelectric materials; polymer materials such as polyvinylidene fluoride (PVDF) and its copolymers with trifluoroethylene and tetrafluoroethylene, nylons with an odd number of carbons (e.g., PA 7), polyvinylchloride (PVC), polyphenylethernitrile (PPEN) and polyacrylonitrle (PAN), among others; as well as combinations thereof. Piezoelectric and electrostrictive actuators require an applied voltage, and current flow can be limited, allowing the application of necessary voltages without danger of serious injury to a patient.

The electrically actuatable member 430 in FIGS. 13A-B is changed between (a) an uncurled (expanded) state as illustrated in the schematic perspective view of FIG. 14A and (b) a curled (contracted) state as illustrated in the schematic perspective view of FIG. 14B. The electrically actuated member 430 need not be perfectly planar in the less curled state, for example, the electrically actuated member 430 can change from a crescent shape to an inverted crescent shape, from a crescent shape to a circular shape, etc. Electrically actuated members can also be employed which change, for example, from a helical shape to a straight shape, from a circular ring shape to an ovaloid shape, and so forth.

As a result of the change in shape of the electrically actuated member 430, the inflation lumen 420 is transformable between a contracted lumen state as illustrated in FIG. 13B and an expanded lumen state as illustrated in FIG. 13A. For example, the cross-sectional area of the lumen can be expanded by at least 10%, 15%, 20%, 25%, 50%, 75%, 100% or more during the transition from the contracted lumen state to the expanded lumen state. The device 400 is more readily inserted through the body lumen of a patient when in the contracted lumen state of FIG. 13B, as compared to the expanded lumen state of FIG. 13A.

For instance, placing the lumen 420 in the contracted state allows the balloon catheter shaft 400 to take on a reduced delivery profile, thereby enhancing the ability to insert and track the shaft 400 over a guide wire through a body lumen, such as a blood vessel. Once the balloon catheter shaft 400 is inserted to the desired extent (e.g., once the balloon is in place), the cross section of the inflation lumen 420 is expanded/enlarged by changing the state of the electrically actuated member 430 that is disposed within the shaft 400. This transformation allows the balloon to be efficiently inflated and also holds the inflation lumen 420 open during balloon deflation, at which point the lumen typically experiences negative pressures. It is desirable, although not necessary, to select an electrically actuated member 430 that is in a more curled state (see FIG. 13B) in the absence of an applied voltage, thus providing a low-profile state as a built-in failure mode for the shaft.

Numerous variations on the above are possible. For example, the electroactive member 430 of FIG. 14A can be provided with enhanced longitudinal flexibility by creating one or more regions of narrowed cross-section as illustrated, for example, in FIGS. 15A and 15B. Longitudinal flexibility can also be enhanced by replacing the electroactive member 430 of FIG. 14A with a series of electroactive members 430, as illustrated in FIG. 15C. These electroactive members 430 are electrically connected to one another by conductive members (not illustrated), for instance, metallic conductors, such as gold wires.

A further variation is illustrated in FIGS. 16A and 16B, which contain cross-sectional views of a balloon catheter shaft 400 in expanded and contracted profiles, respectively. These figures illustrate an inner wall 414 (i.e. an inner tubular member) defining an inner guidewire lumen 425, and an outer wall 412 (i.e., an outer tubular member), which along with the inner wall 414 defines an annular outer inflation lumen 420.

Analogous to the device of FIGS. 13A and 13B above, the electrically actuated member 430 in FIGS. 16A and 16B is in the form of an elongated strip, which is disposed within the outer wall 412 and which is electrically transformable from one degree of bending to another. As a result of the change in the shape in the electrically actuated member 430, the inflation lumen 420 is transformed between an expanded lumen state in FIG. 16A and a contracted lumen state in FIG. 16B.

As above, the inner wall 414 and outer wall 412 are beneficially fabricated, for example, from a polymer or other flexible material via extrusion or other commercially suitable processes known in the art. The fact that the inner and outer walls 414, 412 are discreet components allows them to be readily constructed from different materials in some embodiments. For example, the inner wall 414 can be fabricated from a material that is stiffer than the material of the outer wall 412. This arrangement resists binding between the guidewire (not illustrated) and the inner wall 414 during operation, while at the same time allowing the outer wall 412 to readily change shape under the influence of the electrically actuated member 430.

In the cross sections illustrated in connection with the embodiments of FIGS. 13A, 13B, 16A and 16B, only a single electrically actuated member 430 is present in radial cross-section. However, in various other embodiments, one, two, three, four, five, six seven, eight or more electrically actuated members are longitudinally disposed within the device 400 at a given cross-section. For example, the embodiment of the invention illustrated in FIGS. 17A and 17B employs eight electrically actuated members 430, which are disposed around the circumference of the outer wall 412. As a result of the change in shape of the electrically actuated members 430, the inflation lumen 420 is transformed from an expanded lumen state in FIG. 17A to a contracted (or "crinkled") lumen state in FIG. 17B, and vice versa.

In some embodiments of the invention, the electrically actuated member(s) are disposed along the entire length of the inflation lumen. In other embodiments, the electrically actuated member(s) are disposed along only a portion of the length of the inflation lumen. For instance, the electrically actuated member(s) may be disposed only along the insertable portions of the inflation lumen, or they may be disposed only along the distal portions of the inflation lumen that are required to pass through body lumens (e.g., blood vessels) of relatively small cross-section.

Moreover, the electrically actuated member(s) may be disposed along the complete/partial length of the inflation lumen in a variety of configurations, including straight down the complete/partial length of the inflation lumen, helically wound around the complete/partial length of the inflation lumen 420, and so forth.

It is noted that the electrically actuated member(s) 430 in the embodiments of FIGS. 13A-B, 16A-B and 17A-B are disposed within the outer wall of the device between the inflation lumen and the exterior of the device. However, the electrically actuated member(s) could just as readily be disposed on the inside surface or the outside surface of the outer wall.

It is further noted that the device need not be provided with a single inflation lumen as illustrated in FIGS. 13A-B, 16A-B and 17A-B and 17B, but can also be provided with two inflation lumens, three inflation lumens, four inflation lumens, and so forth, either with or without a guidewire lumen.

The above concepts apply to essentially any device for which it is desirable to switch between a first cross-section of relatively reduced area and a second cross-section of relatively expanded area. For examples, in addition to shafts for balloon catheters, the above concepts are applicable to any number of additional devices, including stents, aortic grafts and vena cava filters, among devices.

Figure 18:
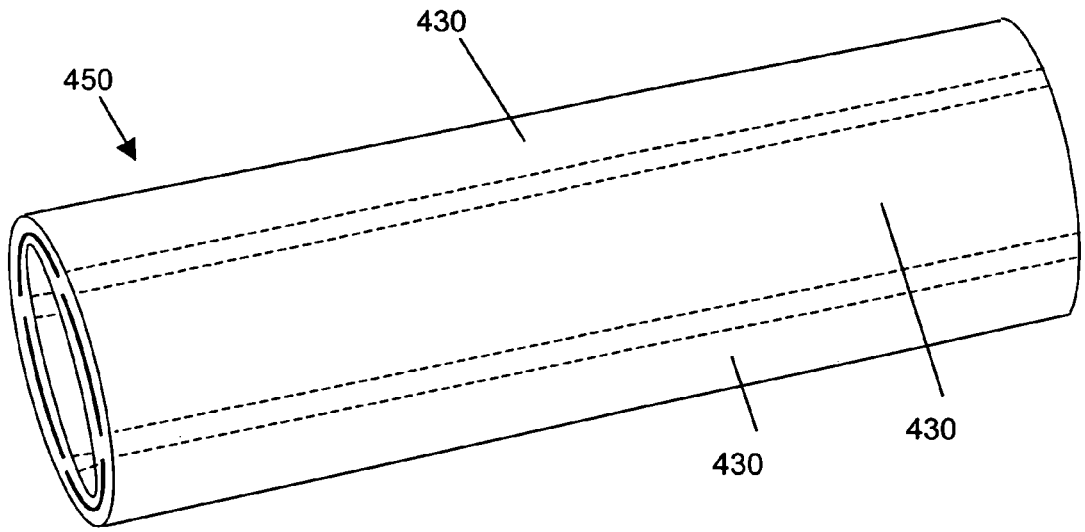
FIGS. 18 and 19 are schematic perspective views of stents, in accordance with two embodiments of the present invention.

For example, a stent 450 is illustrated in FIG. 18 in accordance with an embodiment of the present invention. Within the walls of the stent 450 are provided four electrically actuated members 430. As with the devices of FIGS. 13A-B, 16A-B, and 17A-B above, the electrically actuated members 430 for use in this device include members based on electro-active polymer and piezoelectric materials. Also as above, the electrically actuatable members 430 of FIGS. 18A and 18B are electrically transformable between states having differing degrees of bending. As a result of the change in shape of the electrically actuated members 430 (and analogous to FIGS. 17A and 17B above), the stent 450 is transformable between an expanded state and a contracted state (not shown).

The stent 450 may be permanent or removable. For example, in accordance with certain embodiments of the invention, a voltage is applied to the stent to place it in a reduced profile state. (The electrically actuated members are beneficially selected in this embodiment such that the stent is in a reduce profile state upon application of electrical potential and an expanded profile state when the potential is removed.) In some instances, a delivery sheath (not shown) may be placed over the stent while it is in a reduced profile state to keep it compressed, even if the voltage is removed. Subsequently, the stent is advanced through a body lumen of a patient using a catheter-type delivery system with appropriate electrical contacts for applying a voltage/current to the electrically actuated members. Once the stent reaches the desired destination, the sheath is retracted, if present, while a voltage is applied to the electrically actuated members 430 to maintain the stent 450 in a low profile state. The voltage is then removed to deploy (expand) the stent 450 within the body lumen, and the delivery system is retracted from the patient. The stent 450 then remains in this expanded profile state in the patient unless and until a sufficient voltage is applied to the electrically actuated members (for example, in the event the stent is to be withdrawn from the patient).

Figure 19:
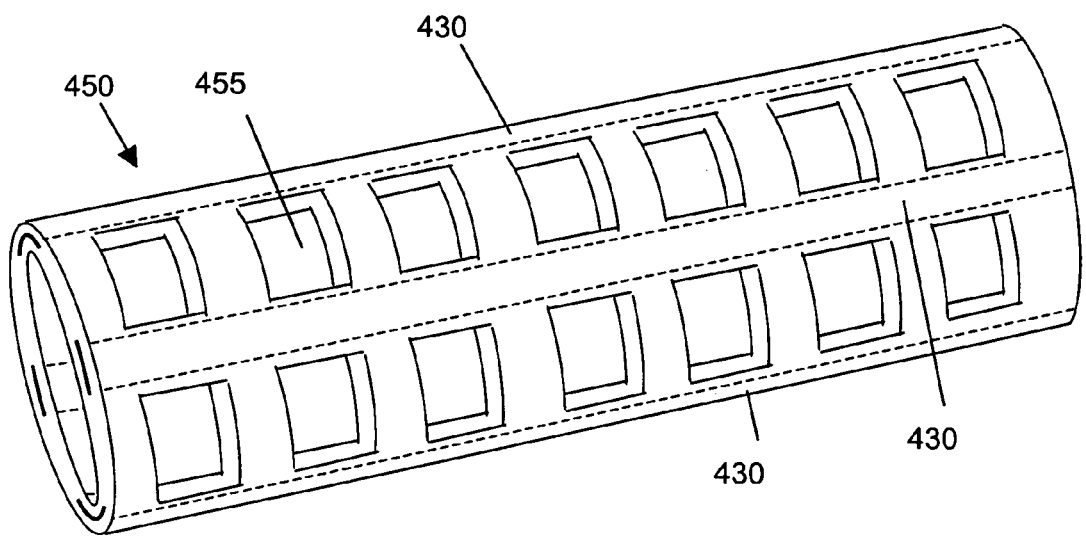

In FIG. 18, the electrically actuated members 430 are disposed within a stent having solid tubular structure. However, as illustrated in FIG. 19, in some embodiments of the invention, it is desirable to utilize a stent 450 that contains a number of windows 455 (one numbered). Like the stent of FIG. 18, four electrically actuated members 430 are provided within the walls of the stent 450, and the stent 450 is electrically transformable between a low profile state and an expanded profile state.

Although the stents 450 of FIGS. 18 and 19 contain four substantially rectangular, electrically actuated members 430, like the balloon catheter shafts 400 above, these devices can include practically any number of electrically actuated members 430 in a wide variety of shapes.

As noted above, the electrically actuated members within the stents and balloon catheter shafts described above (as well as other devices in accordance with the invention) can be formed from various materials, including ceramic materials, metallic materials and polymeric materials. One advantage of metallic electrically actuated members is that the members can be insert-molded (i.e. injection molded) within a polymer structure to form a stent or other tubular member without additional processing.

An advantage of the stents and balloon catheter shafts described above (as well as other reduced-devices in accordance with the invention) is that they can be constructed to expand in two dimensions, rather than three dimensions. Consequently, there would be essentially no foreshortening of the devices and thus no inherent tendency to move or shift position while being deployed.

Figure 12:
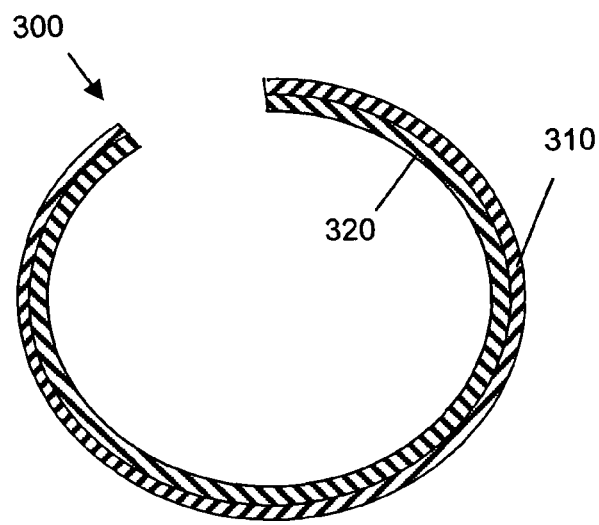
FIG. 12 is a schematic, partial, longitudinal cross-sectional view of an aneurysm coil in accordance with an embodiment of the present invention.

Still other aspects of the present invention are directed to aneurysm filler coil devices. FIG. 12 is a schematic, cross-sectional view, taken along a portion of the length of an aneurysm filler coil device 300. The device 300 comprises an elongate coil member 310 and an elongate active region 320, which comprises an electroactive polymer. The coil member 310 and the active region 320 in the embodiment illustrated are in the form of two elongated strips, forming a bilayer device. In the embodiment illustrated, upon insertion of the coil device 300 into an aneurysm, the active region 320 is contracted, further tightening the coil device 300 and allowing the packing density of the aneurysm to be increased.

In accordance with one specific embodiment, the coil member 310 of the device 300 of FIG. 12 is a platinum member like those found in presently known aneurysm coils. In this case, the platinum coil member 320 also acts as an electrode contact for the active region 320 of the device 300. The active region 320 is selected such that (a) when it is inserted into the body lumen while applying an appropriate potential, the active region 320 is in a expanded state, and (b) when the potential is discontinued (e.g., when the coil is separated from an associated catheter delivery device), the active region 320 shrinks, thereby tightening the coiling of the device 300. If desired, a counter electrode can be provided, for example, in connection with the catheter delivery device, and the surrounding physiological fluid can be used as a sink (electrolyte) for the small ions that exit the active region 320 during shrinkage.

Of course, other aneurysm filler coil configurations are possible in addition to those described above. For example, an alternative aneurysm filler coil device can be formed by wrapping a conductive coil member in a helical fashion with an active member. In other embodiments, the coil device contains an active region that results in coil tightening upon expansion, rather than contraction.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A balloon catheter for expanding a stent, comprising:
   a catheter shaft adapted for insertion into a body lumen of a patient, said catheter shaft defining an inflation lumen;
   an inflatable balloon disposed about a distal region of said catheter shaft, wherein the interior of said inflatable balloon is in fluid communication with said inflation lumen;
   one or more electrically actuated members disposed in a recess formed in the distal region of said catheter shaft, wherein each of said one or more electrically actuated members is a circumferential band disposed around the catheter shaft, radially positioned between said catheter shaft and said inflatable balloon such that an inner surface of the one or more electrically actuated members is attached to an outer surface of the catheter shaft and an outer surface of the one or more electrically actuated members is configured to be in contact with an inner surface of the inflatable balloon, wherein, when activated, said one or more electrically actuated members radially expand such that the outer surface of the one or more electrically actuated members contacts the inner surface of the inflatable balloon and transforms said inflatable balloon from a radially contracted state in which said balloon catheter is more readily insertable into said body lumen of said patient to a first radially expanded state, wherein said one or more electrically actuated members are electroactive polymer actuators, wherein said inflatable balloon is configured to be further expanded to a second radially expanded state with an inflation media received via the inflation lumen, wherein the second radially expanded state is larger than the first radially expanded state;
   a proximal marker and a distal marker, wherein the one or more electrically actuated members are positioned longitudinally between the proximal marker and the distal marker, wherein the proximal marker and the distal marker are disposed around the catheter shaft beneath the inflatable balloon; and
   a stent associated with the inflatable balloon, wherein transforming said inflatable balloon from the radially contracted state to the first radially expanded state with the one or more electrically actuated members expands the stent outwardly from a fully crimped state.

2. The balloon catheter of claim 1, wherein said one or more electrically actuated members comprises a single electrically actuated member.

3. The balloon catheter of claim 1, wherein said one or more electrically actuated members comprises a plurality of electrically actuated members.

4. The balloon catheter of claim 1, wherein said catheter shaft is an extruded body.

5. The balloon catheter of claim 1, wherein said catheter shaft further defines a guidewire lumen.

6. The balloon catheter of claim 1, further comprising a sealed structure that encloses said electroactive polymer actuators, an electrolyte and a counter electrode.

7. The balloon catheter of claim 1, wherein the proximal marker and the distal marker are configured to have an outer diameter that is greater than the outer diameter of the one or more electrically actuated members when the one or more electrically actuated members are in a non-activated state.

* * * * *